(12) United States Patent
Abu-Mulaweh et al.

(10) Patent No.: US 11,219,472 B2
(45) Date of Patent: Jan. 11, 2022

(54) POLY-AXIAL IMPLANT FIXATION SYSTEM

(71) Applicant: Nexxt Spine, LLC, Noblesville, IN (US)

(72) Inventors: Alaedeen Abu-Mulaweh, Noblesville, IN (US); Austin Clemens, Indianapolis, IN (US); Andrew Elsbury, McCordsville, IN (US)

(73) Assignee: Nexxt Spine. LLC, Fishers, IN (US)

( * ) Notice: Subject to any disclaimer, the term of this patent is extended or adjusted under 35 U.S.C. 154(b) by 204 days.

(21) Appl. No.: 16/514,284

(22) Filed: Jul. 17, 2019

(65) Prior Publication Data

US 2020/0237409 A1 Jul. 30, 2020

Related U.S. Application Data

(60) Provisional application No. 62/797,600, filed on Jan. 28, 2019.

(51) Int. Cl.
*A61B 17/70* (2006.01)
*A61B 17/86* (2006.01)

(52) U.S. Cl.
CPC ...... *A61B 17/7037* (2013.01); *A61B 17/7032* (2013.01); *A61B 17/8685* (2013.01)

(58) Field of Classification Search
CPC ............ A61B 17/8685; A61B 17/7037; A61B 17/7032; A61B 17/7034; A61B 17/7035; A61B 17/7038; A61B 17/704
See application file for complete search history.

(56) References Cited

U.S. PATENT DOCUMENTS

| | | | | |
|---|---|---|---|---|
| 9,480,517 | B2 * | 11/2016 | Jackson | A61B 17/7005 |
| 2007/0270813 | A1 * | 11/2007 | Garamszegi | A61B 17/7037 606/278 |
| 2008/0140135 | A1 * | 6/2008 | Konieczynski | A61B 17/7037 606/309 |
| 2010/0023061 | A1 * | 1/2010 | Randol | A61B 17/7037 606/278 |
| 2010/0137920 | A1 * | 6/2010 | Hammill, Sr | A61B 17/7034 606/308 |
| 2010/0145394 | A1 * | 6/2010 | Harvey | A61B 17/7038 606/302 |
| 2016/0296256 | A1 * | 10/2016 | Chandanson | A61B 17/7037 |
| 2017/0333085 | A1 * | 11/2017 | Jackson | A61B 17/863 |

* cited by examiner

*Primary Examiner* — Julianna N Harvey
*Assistant Examiner* — Holly Joanna Lane
(74) *Attorney, Agent, or Firm* — Maginot, Moore & Beck, LLP (57) ABSTRACT

A fixation system includes an elongated rod, a fastener, a yoke, and an insert. The fastener includes a head with a truncated top portion. The yoke receives the rod and includes a yoke opening and a yoke cavity. The yoke cavity supports the head allowing for angular movement of the fastener. The insert is inserted into the yoke above the fastener and includes an insert base and a plurality of prongs. The insert base defines a base cavity that provides clearance for the head. The prongs extend away from the insert base and contact the head of the fastener below the truncated top portion. At least one set of the prongs has a length such that when the fastener is moved to a position of maximum angular movement within the yoke, at least one of the prongs is out of contact with the head of the fastener.

10 Claims, 11 Drawing Sheets

POLY-AXIAL IMPLANT FIXATION SYSTEM

PRIORITY CLAIM

This application claims priority to provisional application No. 62/797,600, filed on Jan. 28, 2019, entitled "Poly-axial implant fixation system," and incorporates herein the disclosure of said application in its entirety.

TECHNICAL FIELD

The present disclosure relates to implant fixation systems, and particularly to systems for engaging an elongated member, such as a spinal rod, to a bone. The disclosure further pertains to a system utilizing a poly- or multi-axial bone fastener.

BACKGROUND

It is common in many orthopaedic procedures to install surgical implants in order to stabilize bones or correct skeletal deformities. In one type of orthopaedic stabilization system, an elongated stabilization member, such as a spinal rod or plate, is attached to a spinal segment of the spinal column in order to align, adjust, or stabilize the spinal segment. A bone engaging member can be utilized to fix the rods or plates to the adjacent vertebrae of the spinal segment. The bone engaging member is typically a hook configured to engage certain portions of the vertebral anatomy, or a bone screw adapted to be threaded into vertebral bone. In the case of a bone screw, the screw is typically screwed into the vertebrae posteriorly.

In such orthopaedic stabilization systems, and most particularly in spinal systems, there is a need to accommodate various angular orientations between the elongated stabilization member and the spinal segment. This necessarily requires an ability to achieve variable angles between the bone engaging member and the elongated stabilization member. In the simplest case, the variable angle is in a single plane. In more complex cases, multi-axial or poly-axial angular orientations are required. One form of such spinal stabilization systems utilizes a bone screw having a generally spherically-shaped head. The screw head is seated within a mating cavity in a yoke. The yoke includes opposite arms forming a U-shaped slot for receipt of a spinal rod above the screw head.

Various mechanisms have been developed to lock the screw head and the rod within the yoke. In one such mechanism, an insert is disposed between the bone screw head and the spinal rod. A set screw threaded into the arms of the yoke presses the rod into the insert, which presses the screw head into the yoke cavity. When fully tightened, the set screw effectively locks all of the components of the stabilization assembly together. The strength or tightness of this fixation requires that all of the components be properly oriented, otherwise no amount of tightening of the set screw will fully lock the assembly together.

During the installation of such stabilization system, the surgeon's ability to visualize the instrumentation is limited because the components of the stabilization system are typically assembled in situ. In particular, it will often become difficult for the surgeon to see the orientation and position of the various components of the stabilization system, thereby hindering the surgeon's ability to confirm proper installation of the stabilization system. Improper installation may lead to further complications, including making necessary adjustments during the surgery, thereby extending the time and cost of the surgery, or possible health concerns for the patient if the improper installation is not corrected during surgery.

Therefore, there is a need for an implant stabilization system that can provide assurances to the surgeon that the components are properly situated so that the components can be effectively locked together when the instrumentation is complete.

SUMMARY

The following is a brief summary of subject matter described in greater detail herein. This summary is not intended to be limiting as to the scope of this disclosure or to the claims.

In at least one embodiment disclosed herein, a fixation system includes an elongated rod, a fastener, a yoke, and an insert. The fastener includes a head and an elongated shank having a bone engaging portion, the head having a truncated top portion defining a top surface. The yoke is configured to receive the elongated rod and includes a yoke opening and a yoke cavity. The yoke opening is configured to receive the elongated shank of the fastener therethrough and the yoke cavity is configured to support the head of the fastener so as to allow for angular movement of the fastener within the yoke opening. The insert is configured to be slidably inserted into the yoke above the fastener and includes an insert base and a plurality of prongs. The insert base defines a rod supporting surface configured to support the elongated rod thereon, and further defines a base cavity opposite the rod supporting surface configured to provide clearance for the head of the fastener when the head is seated within the yoke cavity. The plurality of prongs extends away from the insert base and are configured to contact the head of the fastener below the truncated top portion. At least one set of the plurality of prongs has a length such that when the fastener is moved to a position of maximum angular movement within the yoke, at least one of the plurality of prongs is out of contact with the head of the fastener.

In a further embodiment of the fixation system, movement of the top surface of the head past an end of the at least one prong furthest from the insert base causes at least one of the head of the fastener and the at least one prong of the plurality of prongs to produce a tactile indication to a user.

In another embodiment of the fixation system, movement of the top surface of the head past an end of the at least one prong furthest from the insert base causes at least one of the head of the fastener and the at least one prong of the plurality of prongs to produce an audible indication to a user.

Additionally, in at least one further embodiment of the fixation system, the plurality of prongs includes at least four prongs spaced equidistant around a circumference of the insert.

In some embodiments of the fixation system, the plurality of prongs extend perpendicularly away from a bottom surface of the insert base.

In further embodiments of the fixation system, the plurality of prongs includes at least four first prongs spaced equidistant around a circumference of the insert and at least four second prongs spaced equidistant around the circumference of the insert. The at least four first prongs extend away from the insert base a first distance and the at least four second prongs extend away from the insert base a second distance, wherein the second distance is greater than the first distance.

In other embodiments of the fixation system, a third distance is defined between a center of the head of the fastener and the bottom surface of the insert base, wherein the second distance is less than the third distance.

In at least one further embodiment of the fixation system, each prong of the plurality of prongs includes an interior surface, each interior surface including a prong contour that matches a head contour of an outer surface of the head of the fastener.

In another embodiment of the fixation system, the yoke further includes opposite arms, a yoke base portion, and a surface adjacent to the yoke opening configured to support the head of the fastener. The opposite arms define a yoke slot therebetween, the yoke slot configured to receive the elongated rod. The yoke base portion defines the yoke opening, the yoke opening configured to be in communication with the yoke slot. The yoke further defines a cross bore passing through each of the arms transverse to the yoke slot.

In a further embodiment of the fixation system, the insert base is configured to be slidably inserted between the arms of the yoke. The insert further includes a pair of resiliently deflectable fingers extending from the base to define a base slot configured to receive said rod therebetween, each of the resiliently deflectable fingers including a tab projecting therefrom toward the cross bore of the yoke when the insert is disposed within the yoke. Each tab is configured to be received within a cross bore in a corresponding arm of the yoke.

Additionally, in at least one further embodiment of the fixation system, each tab defines a beveled face configured to bear against the arms of the yoke as the insert is slid into the yoke slot of the yoke. Each beveled face is configured to deflect the respective resiliently deflectable finger toward the other resiliently deflectable finger until the insert is advanced far enough into the yoke for the tabs to align with the cross bores of the yoke so as to lock the tabs within the cross bores.

In another embodiment of the fixation system, the yoke opening and the yoke cavity are configured to allow for spherical angular movement of the fastener within the yoke opening.

In at least one embodiment, an insert for slidably inserting into a yoke of a fixation system includes an insert base and a plurality of prongs. The insert base defines a rod supporting surface configured to support an elongated rod of the fixation system thereon. The insert base further defines a base cavity opposite the rod supporting surface configured to provide clearance for a head of a fastener of the fixation system when the head is seated within a yoke cavity of the yoke. The plurality of prongs extend away from the insert base and are configured to contact the head of the fastener below a truncated top portion of the head. At least one set of the plurality of prongs has a length such that when the fastener is moved to a position of maximum angular movement within the yoke, at least one of the plurality of prongs is out of contact with the head of the fastener. The insert is configured to be slidably inserted into the yoke above the fastener.

In a further embodiment of the insert, movement of the top surface of the head past an end of the at least one prong furthest from the insert base causes at least one of the head of the fastener and the at least one prong of the plurality of prongs to produce a tactile indication to a user.

In another embodiment of the insert, movement of the top surface of the head past an end of the at least one prong furthest from the insert base causes at least one of the head of the fastener and the at least one prong of the plurality of prongs to produce an audible indication to a user.

Additionally, in at least one further embodiment of the insert, the plurality of prongs includes at least four prongs spaced equidistant around a circumference of the insert.

In some embodiments of the insert, the plurality of prongs extend perpendicularly away from a bottom surface of the insert base.

In at least one embodiment of the insert, the plurality of prongs includes at least four first prongs spaced equidistant around a circumference of the insert and at least four second prongs spaced equidistant around the circumference of the insert. The at least four first prongs extend away from the insert base a first distance and the at least four second prongs extend away from the insert base a second distance, wherein the second distance is greater than the first distance.

In at least one embodiment, an assembly for a fixation system includes a yoke, an insert base, and a plurality of prongs. The yoke is configured to receive an elongated rod and includes a yoke opening and a yoke cavity. The yoke opening is configured to receive an elongated shank of a fastener of the fixation system therethrough, and the yoke cavity is configured to support a head of the fastener so as to allow for angular movement of the fastener within the yoke opening. The insert base is configured to be slidably inserted into the yoke above the fastener and defines a rod supporting surface configured to support the elongated rod thereon. The insert base further defines a base cavity opposite the rod supporting surface configured to provide clearance for the head of the fastener when the head is seated within the yoke cavity. The plurality of openings extend away from the insert base and are configured to contact the head of the fastener below a truncated top portion of the head. At least one set of the plurality of prongs has a length such that when the fastener is moved to a position of maximum angular movement within the yoke, at least one of the plurality of prongs is out of contact with the head of the fastener.

The above presents a simplified summary of this disclosure in order to provide a basic understanding of some aspects of the technologies disclosed herein, and is not an extensive or complete overview of such topics. As such, the summary above does not delineate the scope of this disclosure, and is not intended to identify key or critical aspects of the disclosure. Further details are provided by the detailed description, the claims, and the drawings.

DETAILED DESCRIPTION

For the purposes of promoting an understanding of the principles of the embodiments described herein, reference is now made to the drawings and descriptions in the following written specification. No limitation to the scope of the subject matter is intended by the references. This disclosure also includes any alterations and modifications to the illustrated embodiments and includes further applications of the principles of the described embodiments as would normally occur to one of ordinary skill in the art to which this document pertains.

An implant fixation assembly 100 as shown in FIGS. 1A-3 is adapted for use in spinal fixation and stabilization. The implant fixation assembly 100 is similar to the fixation assembly shown in U.S. Pat. No. 10,172,647 (the '647 Patent), issued on Jan. 8, 2019, the entire disclosure of which is incorporated herein by reference.

The implant fixation assembly 100 includes a bone engaging fastener 104, in the form of a bone screw, and a yoke 108 that couples the bone screw 104 to an elongated stabilization member in the form of a spinal rod 112. A set screw 116 is inserted into an open top portion of the yoke 108 in order to clamp the various components, including the bone screw 104, yoke 108, and spinal rod 112, together. The bone screw 104 is capable of being oriented in any one of a plurality of spherical angles relative to the yoke 108. An insert 120 is disposed between the rod 112 and the bone screw 104, as best seen in FIG. 3.

Figure 4:
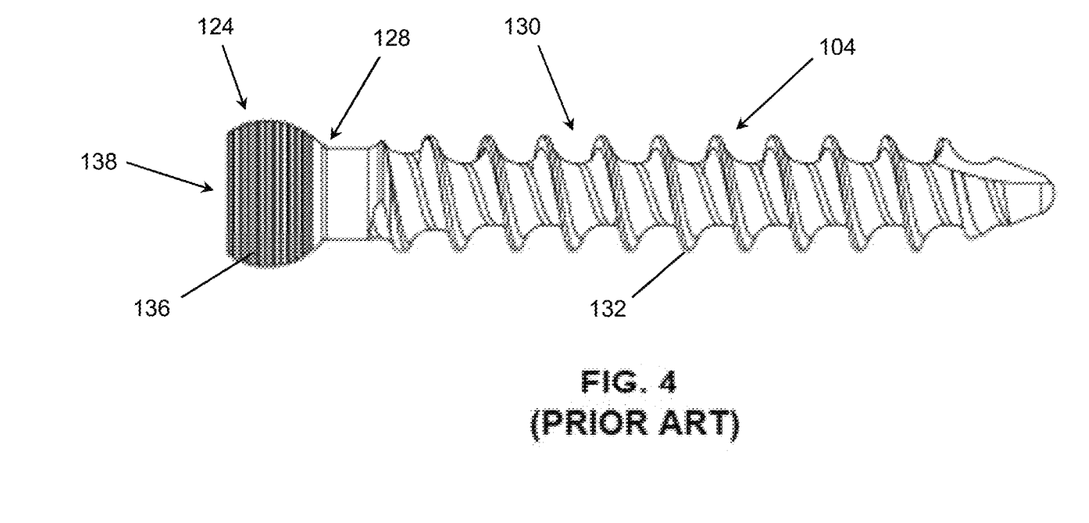
FIG. 4 is a side view of the bone engaging fastener component of the fixation system shown in FIGS. 1A-3.

FIG. 4 shows the bone screw 104 in greater detail. The bone screw 104 includes a generally spherically shaped head 124 that transitions into a smooth shank 128 in a direction toward the main body 130 of the bone screw 104. The smooth shank 128 of the bone screw 104 is provided with bone engaging threads 132 configured for engagement within vertebral bone. The head 124 may be provided with a fixation member 136 to enhance the fixation between the bone screw 104 and the yoke 108. For example, the fixation member 136 may include knurling, a roughened surface, or a pattern of grooves that can engage an inner surface of the yoke 108 when the assembly is tightened.

Figure 2:
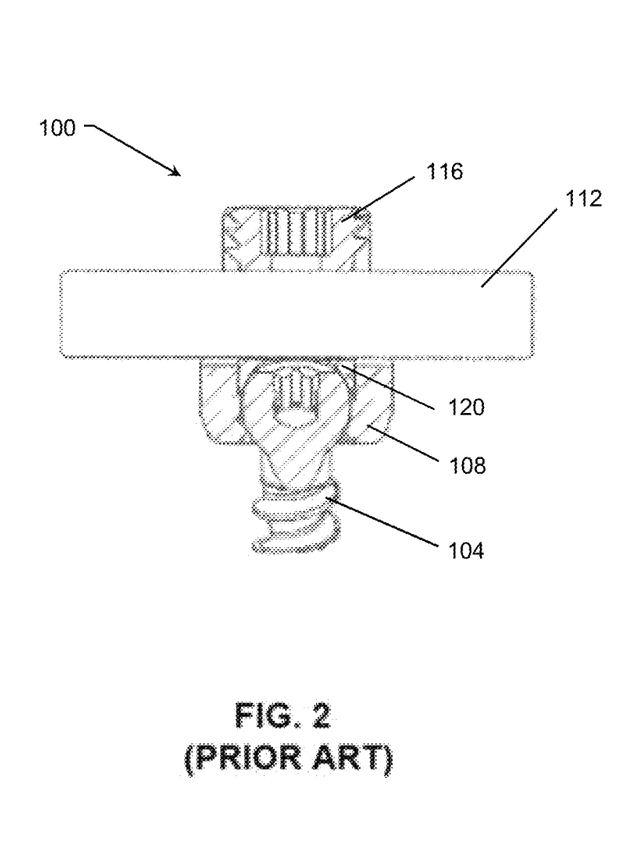
FIG. 2 is a cut-away view of the fixation system shown in FIG. 1A.
Figure 3:
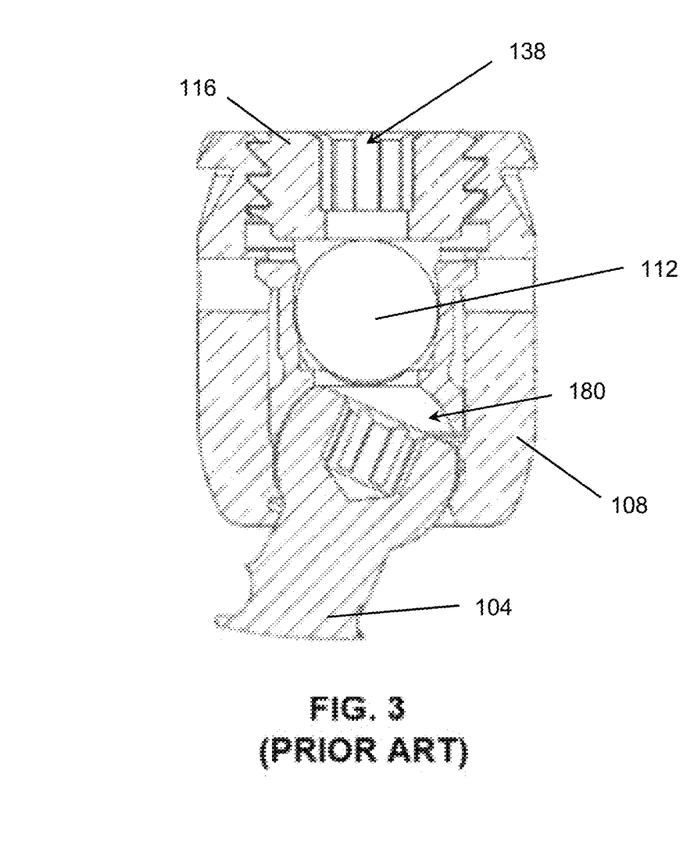
FIG. 3 is an enlarged view of the components of the fixation system shown in FIG. 2.

The head 124 of the bone screw 104 may be provided with a bore 138 in the end of the head 124 facing away from the main body 130 of the bone screw 104 as shown in FIGS. 2 and 3. The bore 138 is configured to receive or mate with a tool to drive the bone screw 104 into the vertebrae. The bore 138 may be configured as a countersink or conical hole in the top of the head 124, an internal hex, a Torx™ configuration, or other similar holes.

Figure 5:
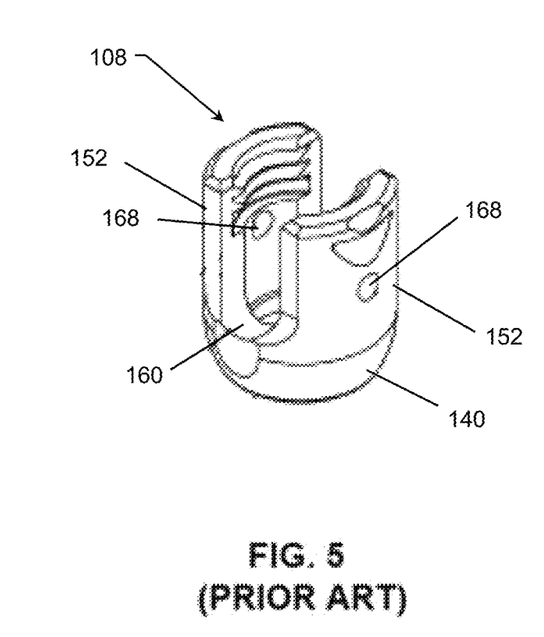
FIG. 5 is a perspective view of the yoke component of the fixation system shown in FIGS. 1A-4.
Figure 6:
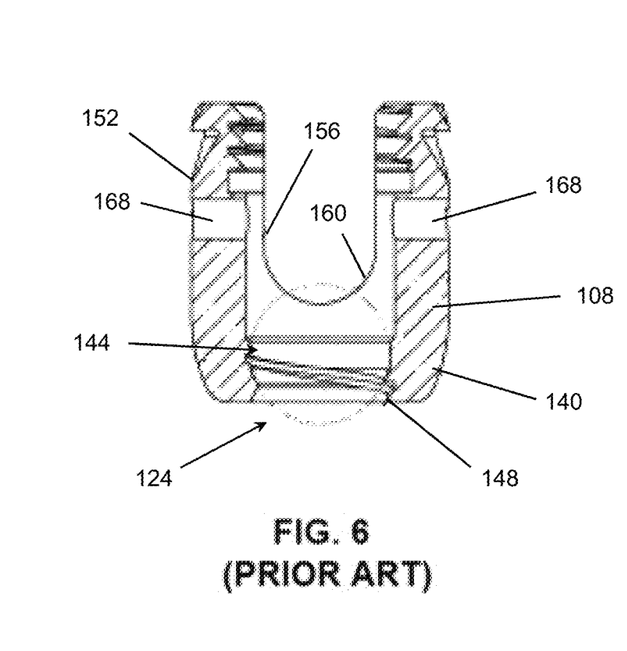
FIG. 6 is a side cross-sectional view of the yoke component shown in FIG. 4.

The yoke 108 is shown in detail in FIGS. 5-6. The yoke 108 includes a base portion 140 that defines a cavity 144 for receiving and supporting the head 124 of the bone screw 104 and a bore 148 through which the shank 128 of the bone screw 104 passes. The cavity 144 and bore 148 may be configured to permit the bone screw 104 to move through a range of spherical angles relative to the yoke 108. However, it is conceivable that the yoke 108 and bone screw 104 may be configured for limited movement relative to each other, such as in a single plane, or configured for no relative movement at all.

The yoke 108 includes a pair of opposite arms 152 defining a central bore 156 adjacent to and in communication with the cavity 144. The arms further define a U-shaped slot 160 configured to receive the spinal rod 112 therein, as shown in FIGS. 1A-1D. In this embodiment, the upper end of the arms 152 may include internal threads 164 configured for threaded engagement with a set screw 116 that is used to clamp the rod 112 within the yoke 108. However, it is conceivable that the set screw 116 may fixedly engage with the arms 152 in other manners known to those skilled in the art. It is also contemplated that other structures may be used to fix the rod 112 within the yoke 108 in lieu of the set screw 116.

The yoke 108 further defines a cross bore 168 passing between each arm 152. The cross bore 168 cooperates with the insert 120 as described herein to provide the surgeon with a sensible indicator that the components are properly oriented when assembled in situ. The cross bore 168 may be further configured for engagement by an insertion tool (not shown) that grasps the yoke 108 in order to facilitate introduction of the yoke 108 and/or bone screw 104.

The insert 120 as shown in FIG. 3 includes a base 172 that defines a generally spherical cavity 180 at the underside of the base 172. The cavity 180 is configured to receive the head 124 of the bone screw 104 so that the head 124 is contained within an upper and lower cavity formed by cooperation between the insert 120 and yoke 108. The spherical features of the yoke 108, insert 120 and bone screw 104 accommodate multi-axial movement of the bone screw 104 relative to the yoke 108. As indicated above, the interface between these components may be configured to limit relative movement accordingly.

The outer diameter of the base 172 of the insert is sized to pass snugly through the central bore 156 in the yoke 108, as shown in FIG. 3. In the illustrated embodiment, the base 172 and central bore 156 are generally cylindrical. However, the components may taper in a conical fashion or assume other complementary configurations that permit sliding movement of the insert 120 along the bore 156. The base defines an opening 176 in communication with the cavity 180 that is sized to receive a tool for allowing a driving tool to be inserted for engagement with the head of the bone screw 104. The insert 120 includes opposite side walls 184 that together with the base 172 define a channel 188 and an insert slot 192. The channel 188 may be generally cylindrical to define a rod supporting surface within which the rod 112 is seated. The insert slot 192 may define a generally curved interior surface 196 to bear against the rod 112 when the rod 112 is seated within the channel 188 and the insert 120 is disposed within the yoke 108. The interface between the rod 112 and the curved surface 196 may incorporate features to enhance engagement of the rod 112 within the insert 120, such as knurling, roughening or other fixation patterns on the rod 112, the curved surface 196, or both.

The insert 120 further includes resiliently deflectable fingers 200 situated between or flanked by the side walls 184. The fingers 200 are attached to the base 172 so that the fingers 200 may deflect relative to the base 172 and to the side walls 184.

The components are assembled as shown in FIGS. 2 and 3 in which the bone screw 104 is passed through the bore 148 in the yoke 108 and is driven into the bone (not shown) a predetermined depth. The yoke 108 is thus initially anchored to the bone, although the head 124 is not yet fixed within the cavity 144, so that the yoke 108 is free to articulate or angulate relative to the bone screw 104 and bone. The spinal rod 112 is placed within the channel 188 of the insert 120 and the insert 120 is then pushed into the central bore 156 of the yoke 108 with the rod 112 aligned with the U-shaped slot 160 of the yoke 108. As the insert 120 passes into the central bore 156, the tab 204 on each resiliently deflectable finger 200 contacts the top of the yoke 108. As the insert 120 is pushed farther into the central bore 156, the tabs 204 force the resiliently deflectable fingers 200 to deflect inward to fully engage the sides of the rod 112. The insert 120 is pushed deeper into the yoke 108 until the tabs 204 reach the cross bores 168 in the yoke arms 152, at which point the resilience of the fingers 200 causes the tabs 204 to deflect outward into the cross bores 168. This action between the resiliently deflectable fingers 200 and the yoke cross bores 168 provides both a tactile and an audible sensory signal that the insert 120 and rod 112 are properly seated within the yoke and over the head 124. The fingers 200 are configured so that the upper surface engages the top of the cross bores 168 to prevent removal of the insert 120, or more particularly to restrict retrograde movement of the insert 120 away from the base portion 140 of the yoke 108.

The cross bores 168 have sufficient depth so that the tabs 204 can translate downward toward the cavity 144 of the yoke 108, as seen in FIG. 3. Thus, when the set screw 116 is threaded into the internal threads 164 of the yoke 108, the set screw 116 bears against the rod 112 seated within the channel 188 of the insert 120. This in turn pushes the insert 120 deeper into the yoke central bore 156 and thereby presses the cavity 180 of the insert 120 into the head 124. The tabs 204 thus translate downward within the cross bores 168 until the beveled face 208 contacts the base of the cross bores 168. As the set screw 116 is threaded further into the yoke 108, the faces of the tabs 204 tend to push the resiliently deflectable fingers 200 inward to engage the rod 112 more tightly. Moreover, an opposite reaction causes the base portion 140 of the yoke 108 to be pulled upward toward the insert 120. When the set screw 116 is fully tightened, the head 124 of the bone screw 104 is thus tightly clamped between the yoke cavity 144 and the insert cavity 180. Moreover, the rod 112 is tightly clamped between the set screw 116 and the channel 188 of the yoke.

Figure 7:
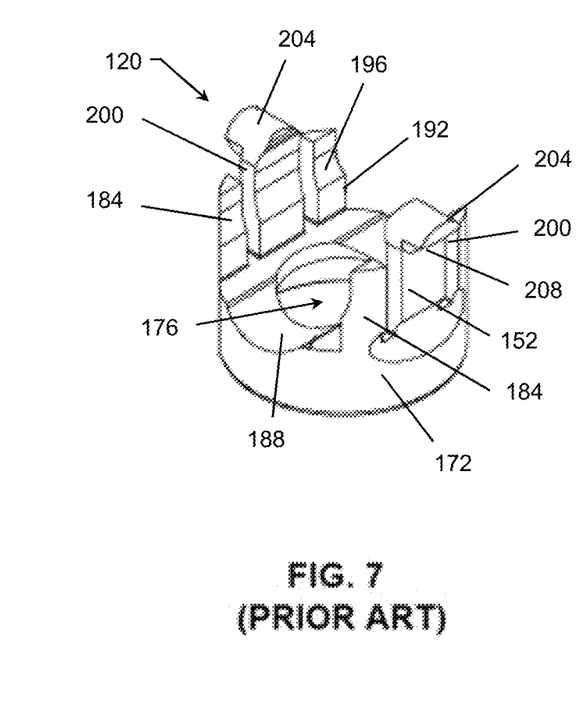
FIG. 7 is a perspective view of the insert component of the fixation system shown in FIGS. 1A-6.
Figure 8:
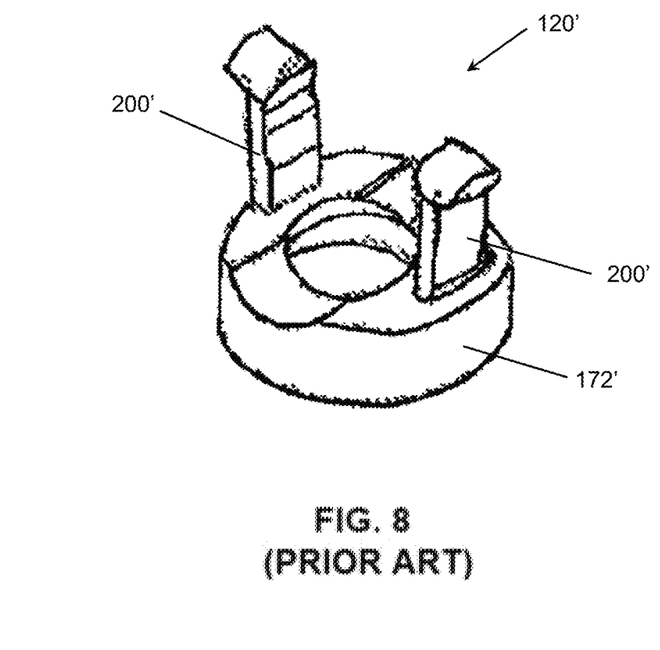
FIG. 8 is a side view of an alternative insert component for the fixation system.
Figure 9:
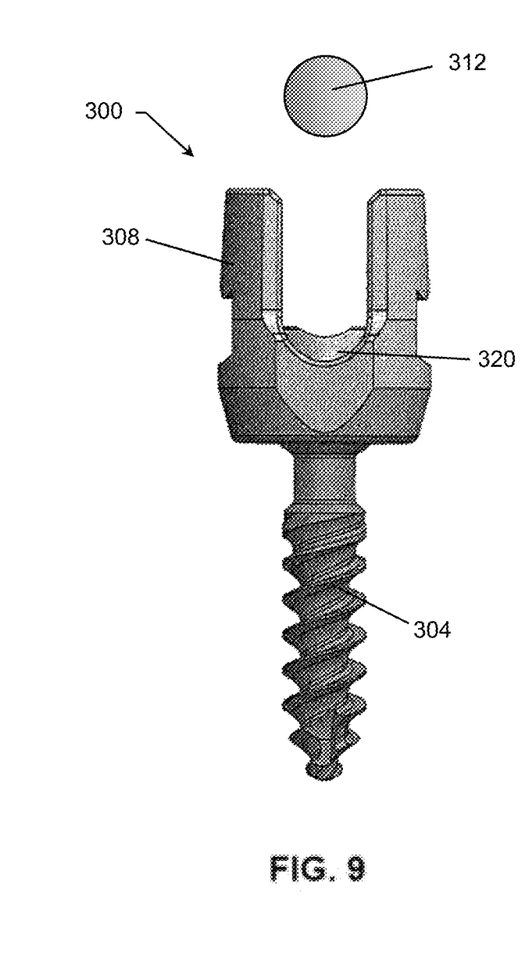
FIG. 9 is a front view of an alternative poly-axial fixation system.

The '647 Patent discloses an alternative insert 120' as shown in FIG. 8. The insert 120' includes resiliently deflectable fingers 200' projecting from the base 172'. In this embodiment, the insert 120' does not include the side walls 184 found in the insert 120 of FIG. 7. Thus, the engagement of the rod 112 is accomplished solely by the resiliently deflectable fingers 200'. The fingers 200' are configured in a similar fashion to the fingers 200 in that the fingers 200' deflect as the insert 120' is positioned within the yoke 108. The insert 120' also defines a cavity (not shown), similar to cavity 180 in FIG. 3, that is configured to receive the head 124 of the bone screw 104 when the components are assembled.

Figure 1A:
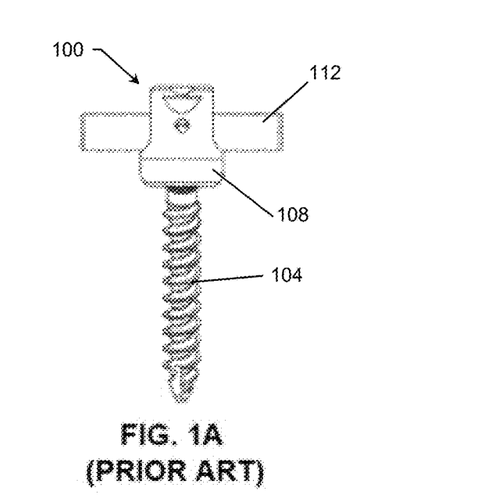
FIG. 1A is a front view of a poly-axial fixation system.
Figure 1B:
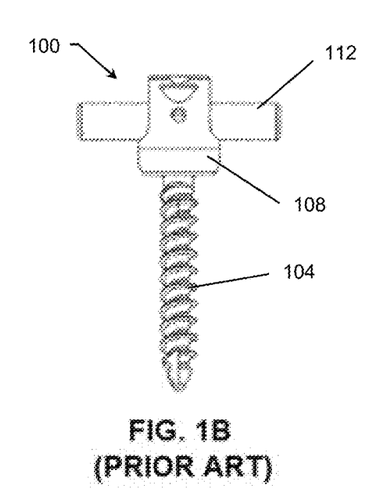
FIG. 1B is a rear view of a poly-axial fixation system.
Figure 1C:
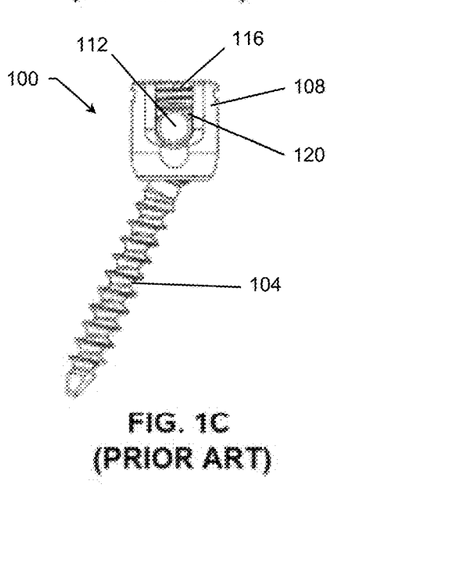
FIG. 1C is a side view of a poly-axial fixation system.
Figure 1D:
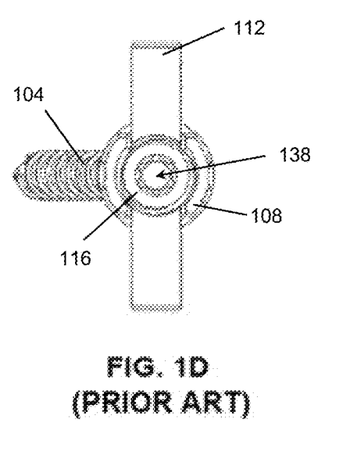
FIG. 1D is a top view of a poly-axial fixation system.

As illustrated in FIGS. 1A-1C, the bone screw 104 can adopt a range of angles relative to the yoke 108, and therefore the rod 112, in multiple planes. The screw 104 position shown in FIG. 1C illustrates the maximum angular extent of movement of the bone screw 104 relative to the yoke 108. As discussed above, since the bone screw 104 is engaged in the body of the patient, such as in a vertebral body, the surgeon does not have direct visualization and/or minimal indication of the orientation of the bone screw 104 relative to the yoke 108. Thus, in at least one embodiment, the insert for the poly-axial implant fixation system provides a notification to the surgeon that the bone screw is at its maximum or full angulation relative to the yoke.

The fixation assembly 300 shown in FIGS. 9-15 includes an insert 320 according to the present disclosure that provides a tactile or auditory indication when the head 324 of the bone screw 304 is at a maximum angle relative to the head 324. The fixation assembly 300 is configured similarly to the fixation assembly 100 described above. In particular, the fixation assembly 300 includes a bone fastening member 304 configured as a bone screw 304 and a yoke 308 that couples the bone screw 304 to an elongated stabilization member in form of a spinal rod 312. A set screw 316 is inserted into an open top portion of the yoke 308 in order to clamp the various components including the bone screw 304, yoke 308, and spinal rod 312 together. Similar to the bone screw 104, the bone screw 304 is capable of being oriented in any one of a plurality of spherical angles relative to the yoke 308, up to and including the maximum angle relative to the head 324 discussed above. An insert 320 is disposed between the spinal rod 312 and the bone screw 304. The bone screw 304 may also be configured similarly to the bone screw 104 as depicted in FIG. 4, including a truncated top portion of the spherical head 324.

With reference to FIGS. 10 and 12-14, the yoke 308 may be configured similarly to the yoke 108. In particular, the yoke 308 includes a base body 340 defining a cavity 344 and a bore 348 for receiving and supporting a head 324 and a shank 328 of the bone screw 304. The cavity 344 and bore 348 may be configured to permit the bone screw 304 to move through a range of spherical angles relative to the yoke 308. For example, a cavity 344 and bore 348 having a larger size and shape would allow for a greater range of motion of the bone screw 304, while a more compact design would decrease the range of motion of the bone screw 304.

The yoke 308 includes a pair of opposite arms 352 defining a central bore 356 adjacent to and in communication with the cavity 344. The arms further define a U-shaped slot 360 configured to receive the spinal rod 312 therein. In this embodiment, the upper end of the arms 352 may include internal threads 364 configured for threaded engagement with the set screw 316 that is used to clamp the rod 312 within the yoke 308. However, it is conceivable that the set screw 316 may fixedly engage with the arms 352 in other manners known to those skilled in the art. It is also contemplated that other structures may be used to fix the rod 312 within the yoke 308 in lieu of the set screw 316.

The yoke 308 further defines a cross bore 368 passing between each arm 352. The cross bore 368 cooperates with the insert 320 as described in detail herein to provide the surgeon with a sensible indicator that the components are properly oriented when assembled in situ. The cross bore 368 may be further configured for engagement by an insertion tool (not shown) that grasps the yoke 308 in order to facilitate introduction of the yoke 308 and/or bone screw 304.

Figure 11:
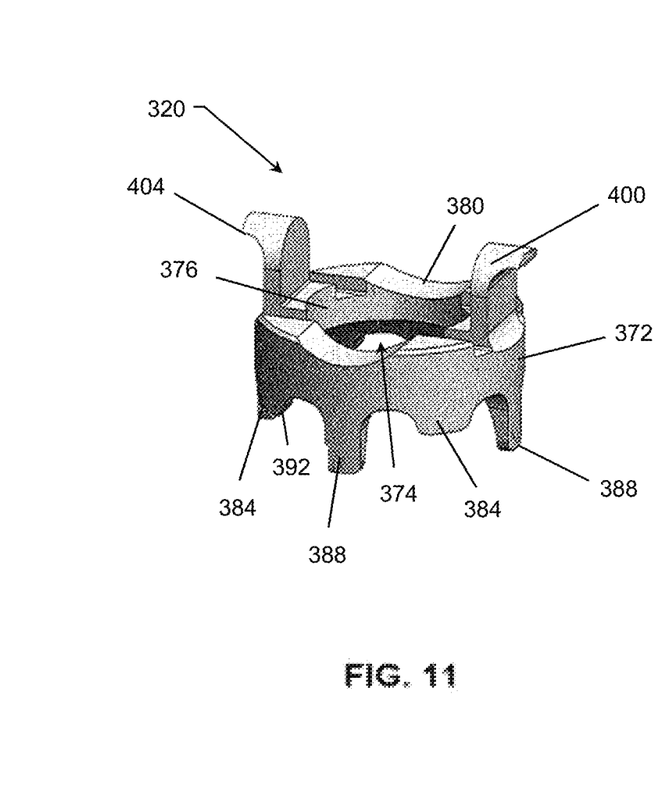
FIG. 11 is a perspective view of the insert component of the fixation system shown in FIGS. 9 and 10.

With reference to FIG. 11, the insert 320 includes a cylindrical body 372 with deflectable fingers 400 configured similar to the body 172, 172' and deflectable fingers 200, 200' of the insert 120, 120' of FIGS. 7 and 8. The body 372 further defines an opening 376 for access to the head 324 of the bone screw 304 and a channel 380 on which the rod 312 is seated when the fixation assembly engages the rod 312 to the bone screw 304. The body 372 also defines a spherical cavity 374 on the underside of the insert 320 that is similar to the cavity 180 of the insert 120 (see FIG. 3). The cavity 374 in the insert 320 thus receives the truncated spherical head 324 at all angular orientations of the bone screw 304 as illustrated in FIGS. 12-15.

As shown in FIG. 11, the fingers 400 of the insert 320 extend away from the cylindrical body 372 in a vertical direction and are located directly opposite one another. In at least one embodiment, the insert 320 may include opposite side walls similar to the side walls 184 of the insert 120 that extend upwardly adjacent to the fingers 400. The walls together with the cylindrical body 372 define the channel 380 and an insert slot similar to the insert slot 192 of the insert 120. The channel 380 may be generally cylindrical to define a rod supporting surface within which the rod 312 is seated. The insert slot may define a generally curved interior surface to bear against the rod 312 when the rod 312 is seated within the channel 380 and the insert 320 is disposed within the yoke 308. The interface between the rod 312 and the curved surface may incorporate features to enhance engagement of the rod 312 within the insert 320, such as knurling, roughening or other fixation patterns on the rod 312, the curved surface, or both.

Similar to the fingers 200 of the insert 120, the fingers 400 are configured to snap into the cross bores 368 formed in the arms 352 of the insert 320. In particular, as shown in FIGS. 12-15, as the insert 320 is pushed into the yoke 308, the tab 404 of the fingers 400 are pushed inwardly, and then, as the tabs 404 of the fingers 400 reach a point even with the cross bores 368, the fingers 400 snap outwardly and lock the insert 320 in place within the yoke 308.

In one feature of the disclosure, the insert 320 includes downward extending first and second prongs 384, 388 that are sized to be received within the central bore 328 of the yoke 308 between the yoke 308 and the head 324 of the bone screw 304, as shown in FIGS. 12-15. The first prongs 384 are shorter than the second prongs 388. In one embodiment, the prongs 384, 388 alternate around the circumference of the body 372 as shown in FIG. 11.

The prongs 384, 388 may be sized and shaped in a variety of manners. In one embodiment, as shown in FIG. 11, the prongs 384, 388 have a generally rectangular shape with beveled or rounded corners facing away from the body 372 of the insert 320. The prongs 384, 388 also include a slightly sloped interior surface such as the contact surface 392 shown in FIGS. 11, 12 and 14. However, in other embodiments, the prongs 384, 388 may include similar polygonal shapes that would be known to those skilled in the art, so long as the configuration of the prongs 384, 388 is conducive to alerting the surgeon to the orientation of the components of the fixation assembly 300. It can also be appreciated that the prongs 384, 388 extend to slightly above the midline or center point of the spherical head 324 of the bone screw 304, at least when the entire assembly is tightened.

In at least the illustrated embodiment, four short first prongs 384 and four long second prongs 388 are provided with the prongs 384, 388 spaced apart at 45° intervals. As shown in FIGS. 12-15, the long second prongs 388 have a length sufficient to provide a contact surface 392 at the end of the second prongs 388 that is in contact with the head 324 of the bone screw 304 at a wide range of angular orientations for the bone screw 304. In contrast, as can also be seen in FIGS. 12-15, the shorter first prongs 384 do not extend as far as the longer second prong 388, but preferably still contact the head 324 of the bone screw 304 closer to the truncated portion of the head 324 at least when the screw 304 is substantially vertically aligned. Preferably, as shown in FIGS. 12-15, the contact surface 392 of each second prong 388 is shaped so as to be flush with the upper, outer surface of the spherical head 324.

Figure 13:
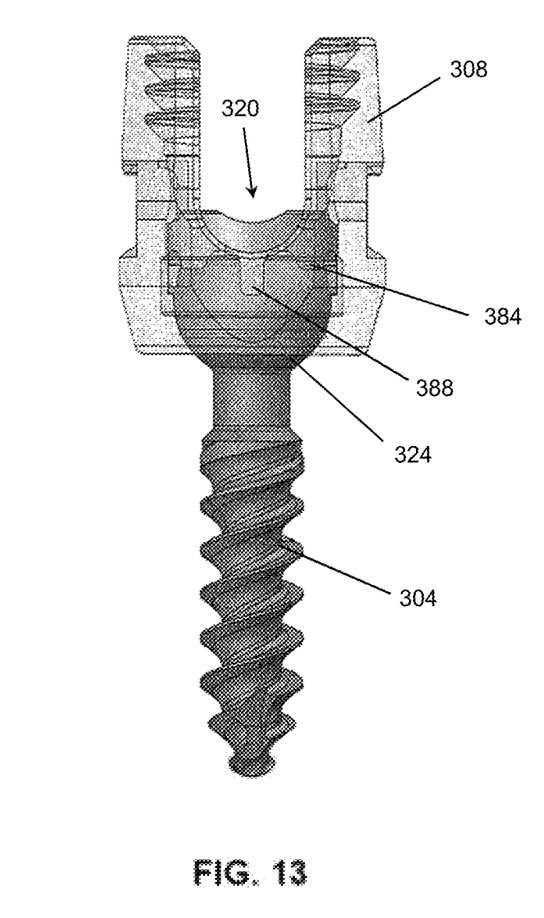
FIG. 13 is a front see-through view of the yoke, fastener and insert components of the fixation system shown in FIGS. 9-11 in their assembled configuration.
Figure 14:
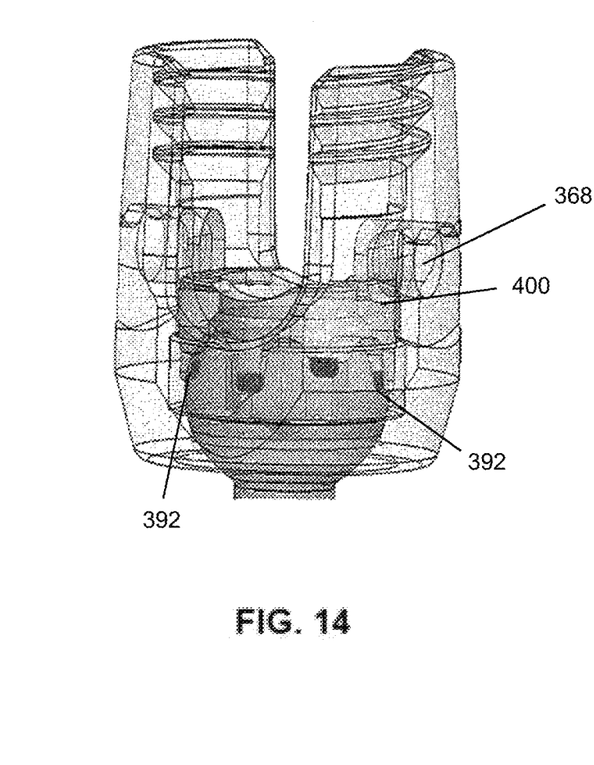
FIG. 14 is a perspective see-through view of the yoke, fastener and insert components of the fixation system shown in FIGS. 9-11 in their assembled configuration.
Figure 15:
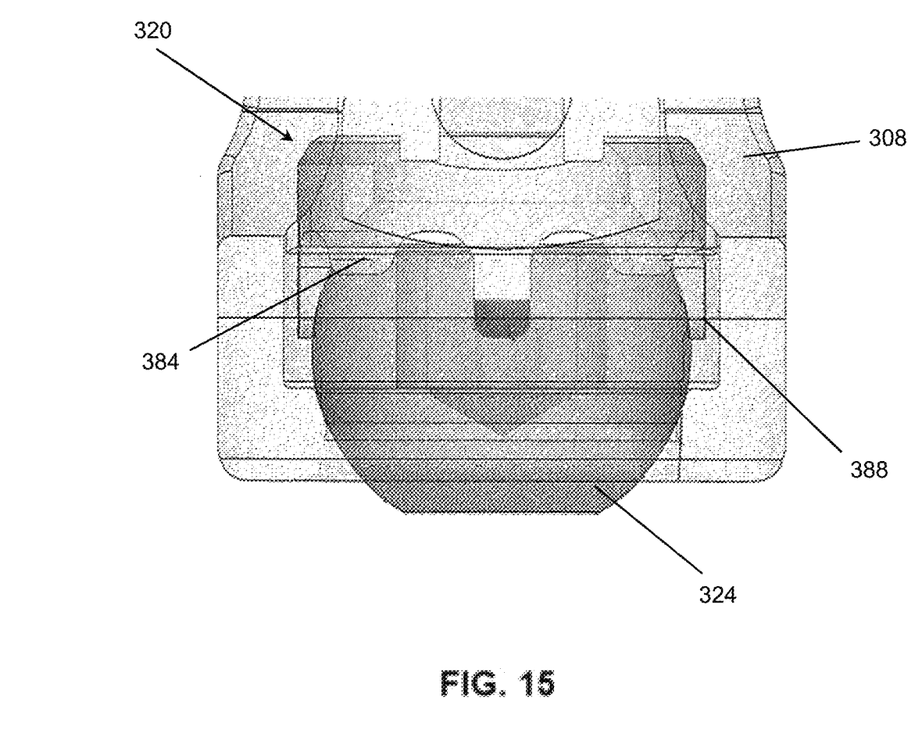
FIG. 15 is a front see-through close-up view of the head of the yoke, head of the fastener, and insert components of the fixation system shown in FIGS. 9-11 in their assembled configuration.

When the bone screw 304 is vertically oriented, as depicted in FIGS. 13-15, the contact surfaces 392 of all four second prongs 388 are flush and in contact with the head 324 of the bone screw 304. It is further noted that the second prongs 388 have a length sized so that the contact surfaces 392 are adjacent, but slightly, above the central diametrical axis of the spherical head 324 of the bone screw 304, at least when the entire assembly is tightened with the screw 304 vertically oriented. The second prongs 388, and therefore the contact surfaces 392, are arranged such that two of the second prongs 388 are substantially oriented along the axial extent of the rod channel 380, and such that the other two second prongs 388 are oriented 90° offset from the axial extent of the rod channel 380. This arrangement of contact surfaces 392 ensures a solid fixation of the bone screw 304 to the yoke 308, and ultimately the rod 312 when the insert 320 is snapped into the yoke 308.

As discussed above, and as seen in FIGS. 13-15, the short first prongs 384 are sized to contact the head 324 of the bone screw 304 closer to the truncated portion of the head 324. The first prongs 384 may also include a slightly sloped interior surface that is contoured to be flush with the upper portion of the head 324 near the truncation surface. The contact surface 392 of the prongs provides a downward force on the top of the screw head 324 when the assembly is tightened.

Figure 12:
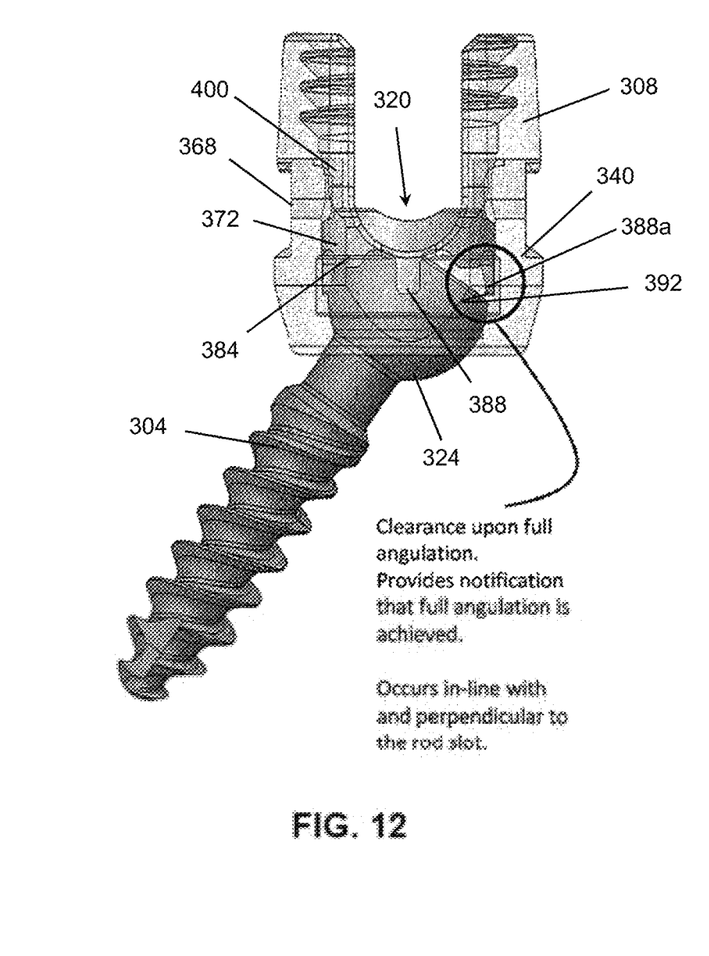
FIG. 12 is a front see-through view of the yoke, fastener and insert components of the fixation system shown in FIGS. 9-11 in their assembled configuration.

In one embodiment of the insert 320, the longer second prongs 388 are sized so that when the bone screw 304 is at its maximum angulation, as depicted in FIG. 12, the truncated top of the head 324 of the bone screw 304 moves beyond the end of at least one of the second prongs 388 (second prong 388a located on the right side of the head 324 when viewing FIG. 12). The movement of the bone screw 304 is limited as the main body 332 of the bone screw contacts the edge wall of the cavity 344 in the bottom of the yoke 308. The left side of the head 324, as can be seen in FIG. 12, moves upwardly into the cavity 344 and in contact with the entire length of opposite second prong 388b.

The movement of the truncated top of the head 324 past the end of the right-most second prong 388a provides an indication to the surgeon that the bone screw 304 has reached its maximum angular extent relative to the yoke 308. For example, in at least one embodiment, the movement of the truncated top of the head 324 past the end of the second prong 388 provides a tactile indication that the top of the head 324 has moved to its maximum angulation. At the same time as the tactile indication, it is possible that the movement creates an audible "click" when the upper edge of the screw head 324 moves free of the end of the second prong 388.

It can be appreciated that in at least one embodiment, four first prongs 384 and four second prongs 388 are oriented at 90° intervals relative to each other. This configuration ensures that the screw head 324 will dislodge from one or two prongs 384, 388 regardless of the angular orientation of the bone screw 304. In other words, if the bone screw 304 is angled along an axis passing through the shorter prongs 384, the truncated edge of the screw head 324 will separate from two of the longer prongs 388 in the same manner depicted in FIG. 15, thereby producing the tactile or audible indication.

It can be appreciated that different configurations of the prongs 384, 388 may be utilized, so long as the movement of the head 324 past the longer second prongs 388 alerts the surgeon that the maximum angulation has been reached. For example, the insert 320 may include more than eight total prongs 384, 388, and thus may be oriented at intervals different than 90° so long as the movement of the head 324 provides at least a tactile and possible an audible "click" when moving past the second prongs 388. Moreover, in at least one embodiment, the outer circumference of the top truncated portion of the head 324 may include a very small lip extending outwardly from the head 324. The lip will thus ensure that a small vibration is produced when the lip moves past the end of the second prong 388. The vibration will be able to be sensed by a surgeon both by sense of touch and possibly audibly depending on the types of materials used. It can also be appreciated that the contact surface 392 of each second prong 388 may include a rough or bumpy surface such that the surgeon can more effectively perceive movement of the head 324 past the end of the second prong 388.

Figure 16:
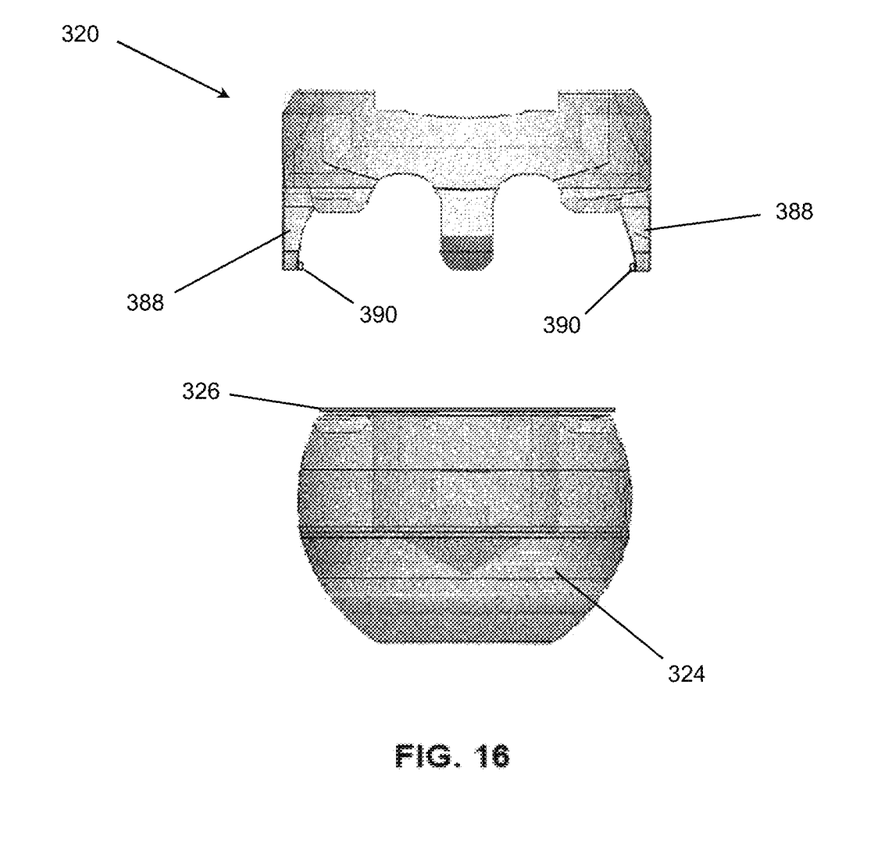
FIG. 16 is an alternative insert component of the fixation system shown in FIGS. 9-11.

In an alternative embodiment shown in FIG. 16, each second prong 388 includes a prong ridge 390, in the form of a small notch or ridge, located at the bottom of the prong 388. The prong ridge 390 is raised off of the contact surface 392 and extends laterally across the contact surface 392. The head 324 of the screw 304 may also include a corresponding head ridge 326 on the outer surface of the head 324 that extends laterally around the entire circumference of the head 324 such that when the head ridge 326 moves past the prong ridge 390, the second prong 388 deflects slightly outwardly until the head ridge 326 passes the prong ridge 390. After the head ridge 326 moves past the prong ridge 390, the second prong 388 snaps back to its original position, producing a vibration that can be felt by the surgeon, as well as possibly an audible sound depending on the materials used.

It can be conceived that each second prong 388 may include multiple prong ridges 390 such that the surgeon may be able to detect when the bone screw 304 passes various angular orientations. For example, each second prong 388 may include two prong ridges 390, one located at the bottom tip of the second prong 388 and the other located at a midpoint between the top and bottom of the second prong 388. As a result, the surgeon can be alerted when bone screw 304 has reached half of its maximum angulation via the head ridge 326 passing the middle prong ridge 390, and then can also be alerted again when the bone screw 304 has reached its maximum angulation via the head ridge 326 passing the bottom prong ridge 390.

In another alternative embodiment, the insert 320 may include only two second prongs 388 arranged on opposite sides of the cylindrical body 372 of the insert 320. As a result, the movement of the bone screw 304 will only produce a tactile or audible alert when the bone screw 304 moves substantially in a single plane.

Figure 10:
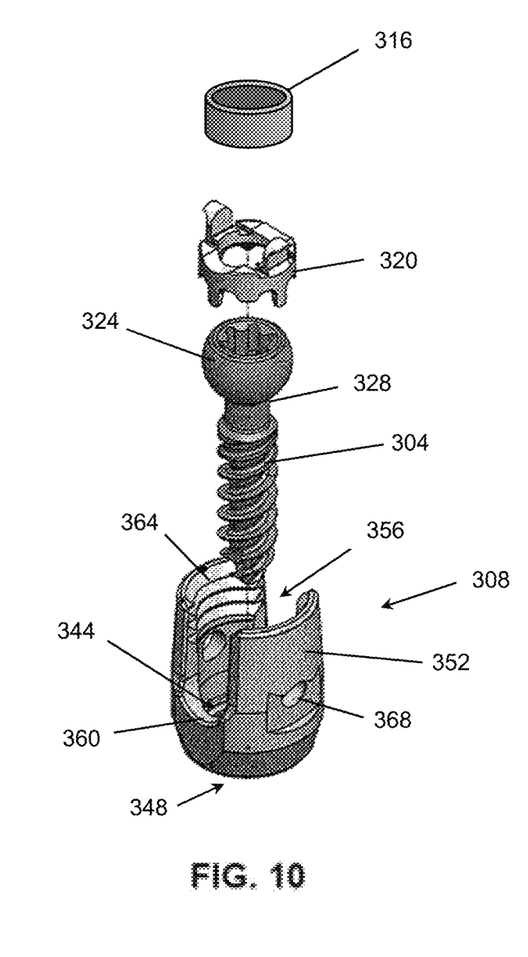
FIG. 10 is an exploded perspective view of the various components of the poly-axial fixation system shown in FIG. 9.

The fixation assembly 300 is assembled similarly to the fixation assembly 100. The components of the fixation assembly 300, in particular the bone screw 304, the yoke 308, the insert 320, and the set screw 316 are shown disassembled in FIG. 10. FIG. 10 also shows the components aligned as they would be prior to assembly. FIGS. 12-15 show the fixation assembly 300 in a fully assembled state without the set screw 316 in order to more clearly illustrate the remaining components of the fixation assembly. In particular, the bone screw 304 is arranged within the bore 348 in the yoke 308, the insert is arranged above the head 324 of the bone screw 304, and the set screw 316 (not shown in FIGS. 12-15) is eventually engaged with the inner portion of the arms 352 of the yoke 308 in order to fully secure the insert 320, and thus the bone screw 304, in place.

Figure 17:
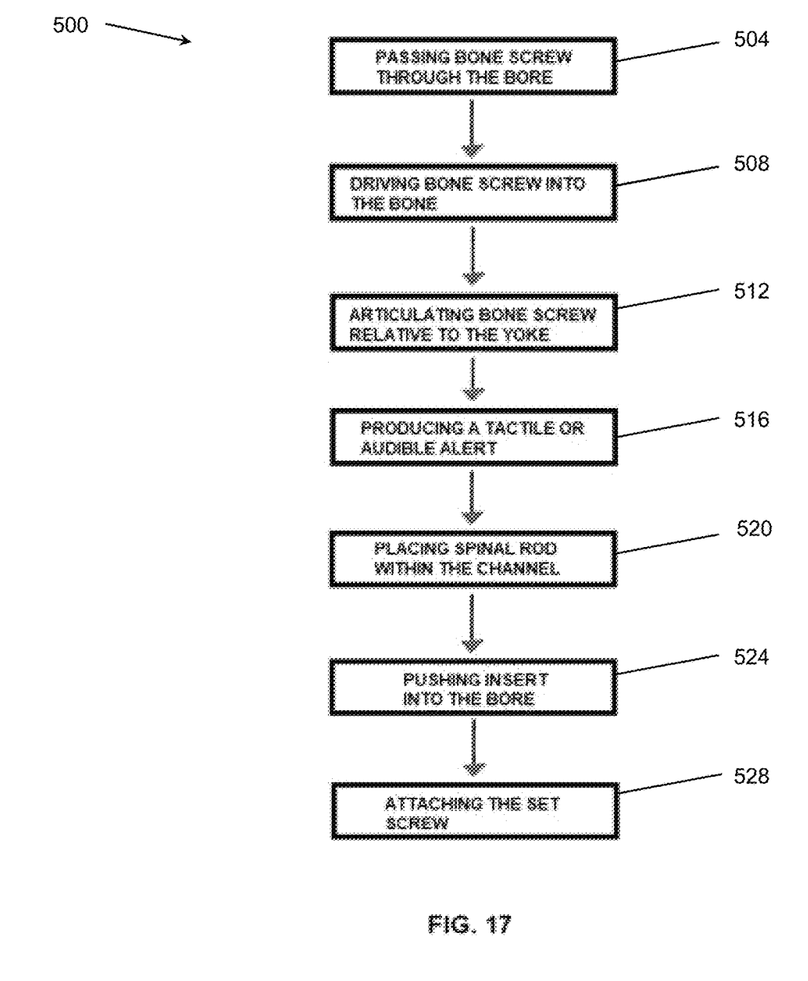
FIG. 17 is a method of assembling and installing the fixation assembly shown in FIGS. 9-11.

A method 500 of assembling and installing the fixation assembly 100, 300 is shown in the flow chart of FIG. 17. The method 500 includes a first step 504 of passing the bone screw 304 through the bore 348 in the yoke 308. In a second step 508, the bone screw 304 is driven into the bone (not shown) a predetermined depth. The yoke 308 is thus initially anchored to the bone, although the head 324 is not yet fixed within the cavity 344. A third step 512 includes articulating or angulating the yoke 308 relative to the bone screw 304 and bone until a desired angle of articulation is reached. If the angle of articulation reached is a maximum articulation of the bone screw, a fourth step 516 includes producing a tactile or audible alert by the top truncated portion of the head 324 moving past the second prong 388. In a fifth step 520, the spinal rod 312 is placed within the channel 380 of the insert 320.

A sixth step 524 includes pushing the insert 320 into the central bore 356 of the yoke 308 with the rod 312 aligned with the U-shaped slot 360 of the yoke 308. During the sixth step 524, as the insert 320 passes into the central bore 356, the tab 404 on each resiliently deflectable finger 400 contacts the top of the yoke 308. As the insert 320 is pushed farther into the central bore 356, the tabs 404 force the resiliently deflectable fingers 400 to deflect inward to fully engage the sides of the rod 312. The insert 320 is pushed deeper into the yoke 308 until the tabs 404 reach the cross bores 368 in the yoke arms 352, at which point the resilience of the fingers 400 causes the tabs 404 to deflect outward into the cross bores 368. This action between the resiliently deflectable fingers 400 and the yoke cross bores 368 provides both a tactile and an audible sensory signal that the insert 320 and rod 312 are properly seated within the yoke 308 and over the head 324. The fingers 400 are configured so that the upper surface engages the top of the cross bores 368 to prevent removal of the insert 320, or more particularly to restrict retrograde movement of the insert 320 away from the base portion 340 of the yoke 308. A seventh step 528 includes attaching the set screw 316.

It is contemplated that the components of the fixation systems described herein are formed of medical grade materials known to those skilled in the art. For example, the various components, including one or more of the screw 104, 304, the yoke 108, 308, the insert 120, 320, and the set screw 116, 316, may be formed of titanium or stainless steel. Titanium, for example, is advantageous in that it may integrate with the vertebrae and is extremely strong but lighter than most alloys. It can be conceived that at least parts of the components may also be comprised of a plastic material, such as polyethylene. Polyethylene, for example, provides both cushioning and greater flexibility of movement of the components. It is further contemplated that the components may be formed by machining, forging or casting in a conventional manner. It is even further conceivable that the components may be formed from 3D-printed biomaterials. Other materials and methods of manufacture may be used as would be known to those skilled in the art, so long as the materials and methods are conducive to alerting the surgeon to the orientation of the components of the fixation assembly 100, 300.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the disclosure.

What is claimed is:

1. A fixation system comprising:
    an elongated rod;
    a fastener including a head and an elongated shank having a bone engaging portion, the head having a truncated top portion defining a top surface;
    a yoke configured to receive the elongated rod and including a yoke opening and a yoke cavity, the yoke opening configured to receive the elongated shank of the fastener therethrough and the yoke cavity configured to support the head of the fastener so as to allow for angular movement of the fastener within the yoke opening;
    an insert configured to be slidably inserted into the yoke above the fastener and including:
        an insert base defining a rod supporting surface configured to support the elongated rod thereon, the insert base further defining a base cavity opposite the rod supporting surface configured to provide clearance for the head of the fastener when the head is seated within the yoke cavity; and
        a plurality of prongs extending away from the insert base and configured to contact the head of the fastener below the truncated top portion, wherein the plurality of prongs includes at least four first prongs spaced equidistant around a circumference of the insert and at least four second prongs spaced equidistant around the circumference of the insert between said at least four first prongs;
        the at least four first prongs extend away from the insert base a first distance, said first prongs having a length at said first distance configured such that when the fastener is moved to a position of maximum angular movement within the yoke, at least one of the first prongs is out of contact with the head of the fastener; and
        the at least four second prongs extend away from the insert base a second distance that is greater than the first distance.

2. The fixation system of claim 1, wherein movement of the top surface of the head past an end of at least one prong of the at least four second prongs, the end being furthest from the insert base, causes at least one of the head of the fastener and the at least one prong of the at least four second prongs to produce a tactile indication to a user.

3. The fixation system of claim 1, wherein movement of the top surface of the head past an end of at least one prong of the at least four second prongs, the end being furthest from the insert base, causes at least one of the head of the fastener and the at least one prong of the at least four second prongs to produce an audible indication to a user.

4. The fixation system of claim 1, wherein the plurality of prongs extend perpendicularly away from a bottom surface of the insert base.

5. The fixation system of claim 1, wherein:
    a third distance is defined between a center of the head of the fastener and the bottom surface of the insert base; and
    the second distance is less than the third distance.

6. The fixation system of claim 1, wherein:
    each prong of the plurality of prongs includes an interior surface; and
    each interior surface includes a prong contour that matches a head contour of an outer surface of the head of the fastener.

7. The fixation system of claim 1, wherein:
    the yoke further includes:
        opposite arms defining a yoke slot therebetween, the yoke slot configured to receive the elongated rod;
        a yoke base portion defining the yoke opening, the yoke opening configured to be in communication with the yoke slot; and
        a surface adjacent to the yoke opening configured to support the head of the fastener; and
    the yoke further defines a cross bore passing through each of the arms transverse to the yoke slot.

8. The fixation system of claim 7, wherein:
    the insert base is configured to be slidably inserted between the arms of the yoke;
    the insert further includes a pair of resiliently deflectable fingers extending from the base to define a base slot configured to receive said rod therebetween, each of the resiliently deflectable fingers including a tab projecting therefrom toward the cross bore of the yoke when the insert is disposed within the yoke; and
    each tab is configured to be received within a cross bore in a corresponding arm of the yoke.

9. The fixation system of claim 8, wherein:
    each tab defines a beveled face configured to bear against the arms of the yoke as the insert is slid into the yoke slot of the yoke; and
    each beveled face is configured to deflect the respective resiliently deflectable finger toward the other resiliently deflectable finger until the insert is advanced far enough into the yoke for the tabs to align with the cross bores of the yoke so as to lock the tabs within the cross bores.

10. The fixation system of claim 1, wherein the yoke opening and the yoke cavity are configured to allow for spherical angular movement of the fastener within the yoke opening.

* * * * *